United States Patent [19]

Warm et al.

[11] Patent Number: 5,344,963
[45] Date of Patent: Sep. 6, 1994

[54] PROCESS FOR THE PRODUCTION OF SUBSTITUTED VINYLBENZENES

[75] Inventors: Aleksander Warm, Visperterminen; David Laffan, Visp, both of Switzerland

[73] Assignee: Lonza Ltd., Gampel/Valais, Switzerland

[21] Appl. No.: 44,166

[22] Filed: Apr. 8, 1993

Related U.S. Application Data

[62] Division of Ser. No. 964,056, Oct. 21, 1992.

Foreign Application Priority Data

Oct. 23, 1991 [CH] Switzerland .................. 3101/91

[51] Int. Cl.$^5$ .................................................. C07C 69/00
[52] U.S. Cl. ........................................ 560/130; 560/138
[58] Field of Search ................ 560/130, 138; 568/716, 568/744

[56] References Cited

U.S. PATENT DOCUMENTS

| | | | |
|---|---|---|---|
| 3,966,801 | 6/1976 | Diamond | 562/496 |
| 4,676,604 | 6/1987 | Petrzilka | 560/138 X |
| 4,956,123 | 9/1990 | Sawada et al. | 560/138 X |
| 5,080,886 | 1/1992 | Mickle et al. | 424/10 |
| 5,142,095 | 8/1992 | Connor et al. | 560/138 X |

OTHER PUBLICATIONS

Manecke et al, Chem. Abs., vol. 54, 5538, (1960).
Chem. Berichte, vol. 92, (1959), pp. 2958 to 2961.

*Primary Examiner*—Arthur C. Prescott
*Attorney, Agent, or Firm*—Fisher, Christen & Sabol

[57] ABSTRACT

A process for the production of substituted vinylbenzenes of the general formula:

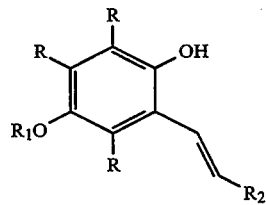

wherein R is a lower alkyl group having 1 to 4 C atoms, $R_1$ is hydrogen or an acetyl group and $R_2$ is hydrogen, a lower alkyl group having 1 to 4 C atoms or a benzyl group. A trialkylhydroquinone is cyclized with an aldehyde to an acetal and the latter is pyrolized to the end product. The substituted vinylbenzenes are valuable intermediate products in the synthesis of antioxidants.

4 Claims, No Drawings

PROCESS FOR THE PRODUCTION OF SUBSTITUTED VINYLBENZENES

This is a divisional application Ser. No. 07/964,056, filed on Oct. 21, 1992.

BACKGROUND OF THE INVENTION

1. Field of the Invention

The invention relates to a process for the production of substituted vinylbenzenes of general formula:

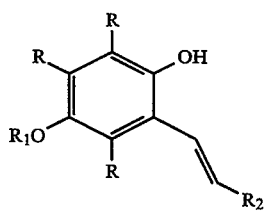

I wherein R is a lower alkyl group having 1 to 4 C atoms $R_1$ is a hydrogen or an acetyl group and $R_2$ is a hydrogen, a lower alkyl group having 1 to 4 C atoms or a benzyl group.

2. Background Art

Substituted vinylbenzenes are valuable intermediate products for the production of antioxidants, such as, of Trolox C ® (U.S. Pat. No. 5,080,886).

It is known from *Chem. Berichte*, Vol. 92, (1959), pages 2958 to 2961 that 1-vinyl-2,4,5-trimethyl-3,6-dihydroxybenzene can be produced over four stages starting from trimethylhydroquinone or trimethylphenol. In such process, especially the last stage, the decarboxylation of 3,6-dihydroxy-2,4,5-trimethyl cinnamic acid proves to be extremely difficult. Thus, the desired vinylbenzene was able to be obtained in a yield of only 4 percent relative to the cinnamic acid derivative used.

BROAD DESCRIPTION OF THE INVENTION

The main object is to provide a process that does not have the above specified drawbacks and with which it is possible to produce the substituted vinylbenzenes on an industrial scale. Other objectives and advantages of the invention are set out herein or are obvious herefrom to one skilled in the art.

The objectives and advantages of the invention are achieved by the process and compounds of the invention.

The invention involves a process for the production of the substituted vinylbenzenes of the general formula:

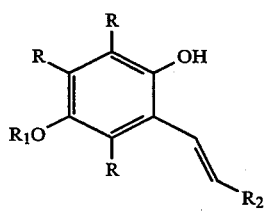

I wherein R is a lower alkyl group having 1 to 4 C atoms $R_1$ is hydrogen or an acetyl group and $R_2$ is hydrogen, a lower alkyl group having 1 to 4 C atoms or a benzyl group. A trialkylhydroquinone of the general formula:

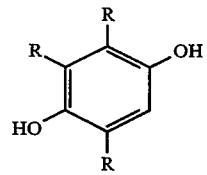

II wherein R has the mentioned meaning, is reacted with an aldehyde of the general formula:

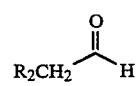

III wherein $R_2$ has the mentioned meaning, in the presence of an acid with exclusion of water to an acetal of the general formula:

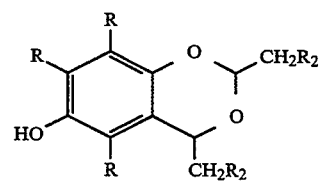

IV wherein R and $R_2$ have the mentioned meanings. This acetal is optionally reacted with acetyl chloride to the acetylated acetal of the general formula:

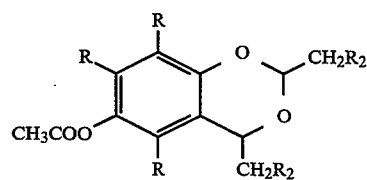

V wherein R and $R_2$ have the mentioned meanings. Finally, the acetal of the general formula IV or V is pyrolized to a vinylbenzene of the general formula:

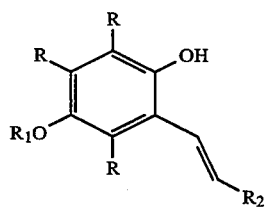

I wherein R, $R_1$ and $R_2$ have the mentioned meanings.

Preferably the trimethyl derivative with R being $CH_3$ is used as the trialkylhydroquinone of the general formula II and the acetylaldehyde with $R_2$ being hydrogen is used as the aldehyde of the general formula III. Preferably the reaction to the acetal of general formula IV is performed at a temperature between $-30°$ to $30°$ C. in the presence of an inert solvent. Preferably hydrochloric acid is used as the acid for the reaction to the acetal of the general formula IV. Preferably the acetylation to the acetal of the general formula V takes place with acetyl chloride in the presence of a tertiary amine at a temperature between 0° and 100° C. Preferably the pyrolysis of the acetal of the general formula IV or V takes place at a temperature of over 300° C. under reduced pressure. Preferably the pyrolysis of the acetal of the general formula IV or V takes place at a temperature between 400° and 500° C. and a reduced pressure between 0.5 and 100 mbar.

The invention also involves acetals of the general formula:

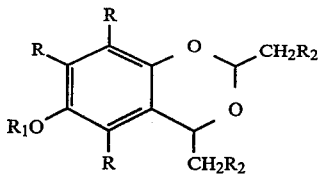

VIII wherein R is a lower alkyl group having 1 to 4 C atoms, $R_1$ is hydrogen or an acetyl group and $R_2$ is hydrogen, a lower alkyl group having 1 to 4 C atoms or a benzyl group. Preferably the acetal of the general formula VIII is 2,4,5,7,8-pentamethyl-4H[1,3]dioxin-ol of the formula:

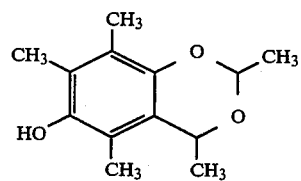

VII

The invention further involves substituted vinylbenzenes of the general formula:

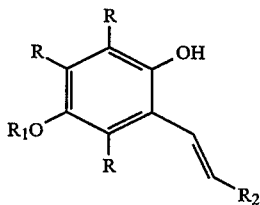

I wherein R is a lower alkyl group having 1 to 4 C atoms, $R_1$ is a hydrogen or an acetyl group and $R_2$ is hydrogen, a lower alkyl group having 1 to 4 C atoms or a benzyl group. Preferably the substituted vinylbenzene of the general formula I is acetic acid-4-hydroxy-2,5-6-trimethyl-3-vinylphenyl ester of the formula:

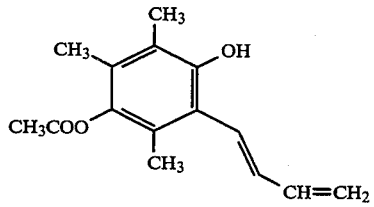

IX

DETAILED DESCRIPTION OF THE INVENTION

According to the invention process, in the first stage, a trialkylhydroquinone of the general formula:

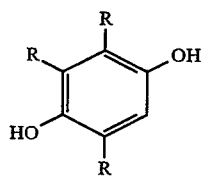

II wherein R has the above-mentioned meaning, is reacted with an aldehyde of the general formula:

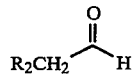

III wherein $R_2$ has the above-mentioned meaning, in the presence of an acid and with exclusion of water to the acetal of the general formula:

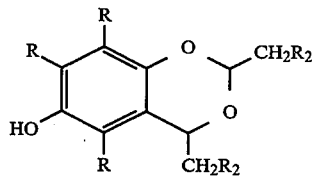

IV wherein R and $R_2$ have the above-mentioned meanings. Preferably trimethylhydroquinone is reacted with acetaldehyde to the corresponding acetal of the general formula IV with R being $CH_3$ and $R_2$ being hydrogen. Suitably the reaction takes place at a temperature between $-30°$ to 30° C. preferably at a temperature under 20° C. in the presence of an inert solvent. Suitably the aldehyde is used in excess. Suitable anhydrous acids are, e.g., hydrochloric acid, hydrobromic acid, sulfuric acid and methanesulfonic acid. Preferably hydrochloric acid is used.

The acetals of the general formula IV resulting in good yields can be isolated from the reaction mixture in ways known in the art.

The acetals of the general formula IV so far have not been described in the prior art and therefore are also part of the invention. The preferred acetal of the general formula IV is the compound with R being $CH_3$ and $R_2$ being hydrogen.

If desired the acetals of the general formula IV can be acetylated to acetylated acetals of the general formula:

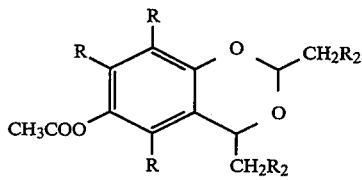

V wherein R and $R_2$ have the above-mentioned meanings. These acetals so far have also not been described in the prior art and, therefore, are also part of the invention. The preferred acetylated acetal of the general formula V is the compound with R being $CH_3$ and $R_2$ being hydrogen.

The acetylation takes place suitably with acetyl chloride in the presence of a tertiary amine, such as, triethyl amine, in a suitable inert solvent. Usually the reaction takes place practically quantitatively at a temperature between 0° and 100° C.

The acetylated acetal can be isolated from the reaction mixture in the usual way and fed to the further reaction (pyrolysis).

In the next stage, the acetals of the general formula IV or V are pyrolyized to the substituted vinylbenzenes of the general formula:

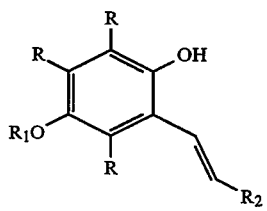

I wherein R, R₁ and R₂ have the above-mentioned meanings. The pyrolysis takes place suitably at a temperature of over 300° C., (up to the highest effective pyrolysis temperature), preferably between 400° and 500° C., at a reduced pressure of between 0.5 and 100 mbar.

Corresponding to the preferred acetals of the general formula IV or V with R being CH₃ and R₂ being hydrogen, the methylated derivatives with R being CH₃, R₁ being hydrogen or acetyl and R₂ being hydrogen resulted as the preferred vinylbenzenes of the general formula I.

The acetylated vinylbenzenes of the general formula I with R₁ being acetyl so far have not been described in the prior art and, therefore, are also part of the invention.

The corresponding vinylbenzenes can be obtained in this way in a good yield of about 70 percent relative to the trialkylhydroquinone used.

EXAMPLE 1

(a) Process for the production of 2,4,5,7,8-pentamethyl-4H-benzene [1,3]dioxin-6-ol Trimethylhydroquinone (60.8 g, 0.4 mol) was suspended in CH₂Cl₂ (11). A solution of acetaldehyde (135 ml, 105.6 g, 1,3 mol) in CH₂Cl₂ (280 ml) was added to this suspension so that the temperature did not exceed 20° C. Then the suspension was saturated with gaseous HCl until the reaction was complete (tracked with TLC, toluene/acetone, 4:1). The suspension gradually dissolved during the HCl-addition. The yellow solution was concentrated by evaporation under vacuum. 83 g (93.7 percent) of yellow solid with a melting point of 101° to 103° C. was obtained. Other data for the product was:

¹H-NMR: (C₆D₆, 300 MHz) δ in ppm 5.21 (q, 1 H, J=7 Hz);
4.87 (q, 1 H, J=6 Hz);
3.78 (s, 1 H);
2.21 (s, 3 H);
1.94 (s, 3 H);
1.69 (s, 3 H);
1.52 (d, 3 H, J=5 Hz);
1.28 (d, 3 H, J=6 Hz);
Isomer: 5.01 (q, 1 H, J=6 Hz );
4.83 (q, 1 H, J=5 Hz);
3.82 (s, 3 H);
1.93 (s, 3 H);
1.78 (s, 3 H); 1.50 (d, 3 H, J=5 Hz); 1.42 (d, 3 H, J-6 Hz).

(b) Process for the production of 1,4-dihydroxy-2,3,5-trimethyl-6-vinylbenzene (2 g, 9.0 mmol) of 2,4,5,7,8-pentamethyl-4H-benzene[1,3]dioxin-6-ol was pyrolized under vacuum (20 mbar) in a quartz tube at 460° C. A light brown solid (1 g, 62 percent) with a melting point of 143° to 145° C. was obtained. Other data for the production was:

¹H-NMR: (CDCl₃, 300 MHz) δ in ppm 6.67 (dd, 1 H, J=12,5 Hz, 19 Hz );
5.68 (d, 1 H, J=12.5 Hz);
5.50 (d, 1 H, J=19 Hz);
5.33 (s, 1 H);
4.25 (s, 1 H);
2.20 (s, 6 H);
2.13 ( s, 3 H).

EXAMPLE 2

(a) Process for the production of acetic acid 2.4,5,7,8-penta-methyl -4H-benzene[1,3]dioxin-6-yl ester 2,4,5,7,8-Pentamethyl-4H-benzene[1,3]dioxin-6-ol (117.4 g, 0.528 mol) and triethylamine (63.14 g, 0.624 mol) were dissolved in CH₂Cl₂ (800 ml) at 0° C. Acetyl chloride (49.0 g, 0.624 mol) was instilled in this solution during 1 hour. This mixture was stirred for 30 minutes and then mixed with water (400 ml). The organic phase was dried with MgSO₄ and concentrated by evaporation under vacuum. A light yellow solid (130.1 g, 93 percent) with a melting point of 91.8° to 92.2° C. was obtained. Other data for the product was:

¹H-NMR: (CDCl₃, 300 MHz) δ in ppm. 5.34 (q, 1 H, J=7.5 Hz);
4.98 (q, 1 H, J=7.5 Hz);
2.35 (s, 3 H);
2.13 (s, 3 H);
2.04 (s, 3 H);
1.95 (s, 3 H);
1.54 (d, 3 H, J=7.5 Hz);
1.52 (d, 3 H, J=7.5 Hz);
Isomer: 5.20 (q, 1 H, J=7.5 Hz);
4.96 (q, 1 H, J=7.5 Hz);
2.35 (s, 3 H);
2.13 (s, 3 H);
2.04 (s, 3 H);
1.99 (d, 3 H);
1.54 (d, 3 H, J=7.5 Hz);
1.47 (d, 3 H, J=7.5 Hz).

(b) Process For The Production of Acetic Acid-4-Hydroxy-2,5,6-trimethyl-3-vinylphenyl ester Acetic acid-2,4,5,7,8-pentamethyl-4H-benzene[1,3]dioxin-6-yl ester (20 g, 75.6 mmol) was pyrolized in a quartz tube at 450° C. under vacuum (10 mbar). After recrystallization from hexane (65 ml), a white solid (14.80 g, 77 percent) with a melting point of 73.5° to 74.8° C. was obtained. Other data for the product was:

¹H-NMR: (CDCl₃, 400 MHz) δ in ppm 6.63 (dd, 1 H, J=11.5 & 18.2 Hz );
5.69 (dd, 1 H, J=1.8 & 11.5 Hz );
5.58 (s, 1 H);
5.51 (dd, 1 H, J=1.8 & 18.2 Hz );
2.32 (s, 3 H);
2.17 (s, 3 H);
2.05 (s, 3 H);
2.01 (s, 3 H).

What is claimed is:

1. A substituted vinylbenzene of formula:

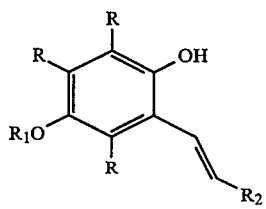

wherein R is a lower alkyl group having 1 to 4 C atoms, $R_1$ is hydrogen or an acetyl group and $R_2$ is hydrogen, a lower alkyl group having 1 to 4 C atoms or a benzyl group, provided that when R is a methyl group, $R_1$ $R_2$ are not hydrogen.

2. Acetic acid-4-hydroxy-2,5-6-trimethyl-3-vinylphenyl ester of formula:

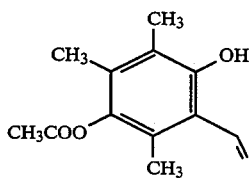

3. A substituted vinylbenzene of formula:

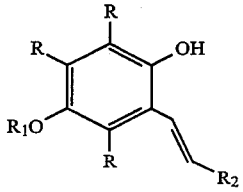

wherein R is a lower alkyl group having 1 to 4 C atoms, $R_1$ is an acetyl group, and $R_2$ is hydrogen, a lower alkyl group having 1 to 4 C atoms or a benzyl group.

4. A substituted vinylbenzene of formula:

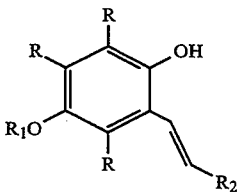

wherein R is a lower alkyl group having 1 to 4 C atoms, $R_1$ is hydrogen or an acetyl group, and $R_2$ is a lower alkyl group having 1 to 4 C atoms or a benzyl group.

* * * * *